United States Patent [19]

Mehdizadeh et al.

[11] 4,020,680

[45] May 3, 1977

[54] APPARATUS AND METHOD FOR DETERMINING CORROSION FATIGUE INHIBITOR EFFECTIVENESS

[75] Inventors: Parviz Mehdizadeh; Burton M. Casad, both of Ponca City, Okla.

[73] Assignee: Continental Oil Company, Ponca City, Okla.

[22] Filed: June 1, 1976

[21] Appl. No.: 691,676

[52] U.S. Cl. .................................. 73/86; 23/253 C
[51] Int. Cl.² ...................................... G01N 17/00
[58] Field of Search ............... 73/91, 86; 23/253 C

[56] References Cited

UNITED STATES PATENTS

| 3,427,873 | 2/1969 | Mehdizadeh | 73/86 |
| 3,504,535 | 4/1970 | Cobb et al. | 73/86 |
| 3,942,546 | 3/1976 | Radd et al. | 73/23 |

*Primary Examiner*—James J. Gill
*Assistant Examiner*—Anthony V. Ciarlante
*Attorney, Agent, or Firm*—Richard W. Collins

[57] ABSTRACT

A cyclically stressed, hollow hydrogen sensor probe for evaluating the corrosion fatigue performance of corrosion inhibitors. A portion of the probe is contained in a jacket having an inlet and outlet for circulating a corrosive fluid containing an inhibitor over the outer surface of the probe. Corrosion at the outer surface of the probe produces hydrogen which permeates to the evacuated inner portion of the probe and produces a current reading in an ion pump in communication with the probe interior, which current reading is indicative of inhibitor performance.

5 Claims, 2 Drawing Figures

APPARATUS AND METHOD FOR DETERMINING CORROSION FATIGUE INHIBITOR EFFECTIVENESS

BACKGROUND OF THE INVENTION

1. Field of the Invention

This invention relates to a method and apparatus for rapidly evaluating the effectiveness of a corrosion fatigue inhibitor on a metal exposed to a corrosive environment while under stress.

Corrosion fatigue is one of the most common causes of oilfield production equipment failure. This failure mechanism is frequently manifested by failure of sucker rods in pumping wells using a sucker rod lift system. The sucker rods of pumping wells are often in contact with corrosive fluids such as brine and/or oil which contains hydrogen sulfide or carbon dioxide. Failure of a sucker rod in a pumping well results in an expensive workover operation and lost production.

The prevailing method of treating sucker rods against corrosion fatigue involves application of a corrosion inhibitor periodically or continuously. A large number of inhibitors are available commercially, and these inhibitors are effective to varying degrees depending upon many factors including the nature of the corrosive fluid in contact with the equipment, the type of material involved, and the conditions of use. While some of the available inhibitors are very effective in certain conditions, it is difficult to predict the effectiveness of a given inhibitor in a particular set of conditions.

2. Description of the Prior Art

The normal method for evaluating the effectiveness of a corrosion inhibitor involves exposing a test specimen of the material to be tested to a corrosive environment for a period of time, and then determining by weight loss the degree of corrosion. It is a relatively simple matter to compare the weight loss of a specimen exposed to a corrosive environment with the weight loss of a similar specimen exposed to the corrosive environment but protected by an inhibitor. However, the results of this type of testing do not accurately correlate with the corrosion fatigue properties of the system under consideration. That is, a corrosion inhibitor may indicate excellent inhibition of corrosion by the weight loss method and yet the material in question, protected by an inhibitor, may fail due to corrosion fatigue at a time similar to or not much different from the time it would have failed if the inhibitor had not been used. This is apparently due to the fact that the type of corrosion which leads to corrosion fatigue failure is localized, and even though the inhibitor protects most of the surface of the material, there is sufficient breakdown of the protective film to allow localized corrosion fatigue cracks to develop, leading to early failure in spite of the presence of an inhibitor.

This discrepancy between the degree of inhibition indicated by the weight loss testing method and the actual corrosion fatigue inhibition has been recognized for some time, and several attempts have been made to obtain corrosion fatigue inhibitor effectiveness data by exposing a specimen of material to be tested to a corrosive environment while dynamically stressing the specimen. One approach to determining the behavior of solid materials exposed to a corrosive environment while the solid materials are being dynamically stressed is described in U.S. Pat. No. 3,427,873. The apparatus and method described in that patent involve repeatedly flexing the material being tested while it is exposed to a corrosive environment. The procedure described in that patent works quite well, but is subject to the deficiency that the test specimen must be tested to failure, which in many cases involves several million cycles, before the performance of the inhibitor in question can be determined.

U.S. Pat. No. 3,504,535 describes an apparatus for simulating and monitoring the stress corrosion condition of a stressed member stored therein by measuring pressure in a tank containing the member.

Corrosion monitoring apparatus including a hydrogen permeable membrane and a getter-ion pump, which apparatus provides a current readout indicative of corrosion rate, is described in detail in U.S. Pat. No. 3,942,546.

There has been a need for a capability of determining the effectiveness of a corrosion fatigue inhibitor by a method which is reliable and can be performed in a short period of time. This invention provides that capability.

SUMMARY OF THE INVENTION

According to the present invention, an apparatus and method for determining the effectiveness of a corrosion fatigue inhibitor are provided. A test probe having an evacuatable chamber is attached at one end to a fixed frame, and at the other end to a device which applies a cyclic fatigue load thereto. A jacket is provided about a part of the test probe, and the jacket is equipped with inlet and outlet facilities for circulating a corrosive fluid over a portion of the test probe. The portion of the test probe covered by the jacket includes the evacuatable chamber, which is in fluid communication with a getter-ion pump. The ion pump is equipped with a current-indicating means which provides an indication of the amount of hydrogen permeating the test probe when a corrosive fluid is circulated over the outer surface of the test probe. This apparatus gives an indication of the amount or rate of fatigue corrosion taking place while the test probe is being dynamically stressed, and the effectiveness of a corrosion fatigue inhibitor can be determined without the necessity of dynamically stressing the test probe to destruction.

It is accordingly an object of this invention to provide an apparatus and method for determining the effectiveness of a corrosion fatigue inhibitor.

It is a further object of the invention to provide such an apparatus and method that will enable the effectiveness of a corrosion fatigue inhibitor to be determined in a short period of time without the requirement of dynamically stressing the test specimen to destruction.

The above as well as additional objects and advantages are provided by this invention, as will be apparent from the following detailed description of the preferred embodiment thereof.

DESCRIPTION OF THE PREFERRED EMBODIMENT

Figure 2:
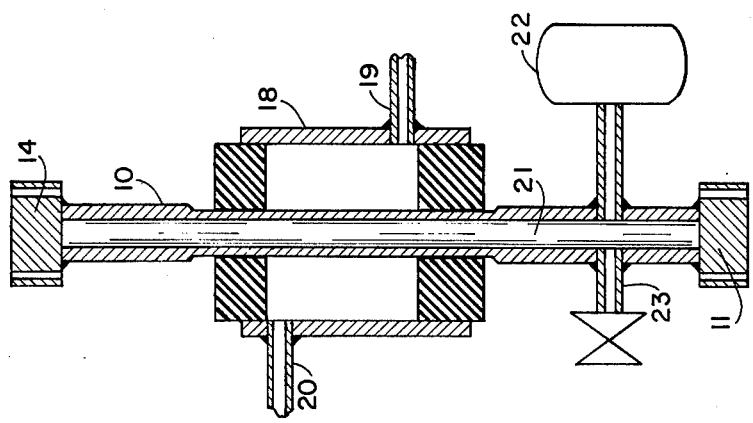
FIG. 2 is a cross section showing the details of a test probe and its associated jacket and ion pump.
Figure 1:
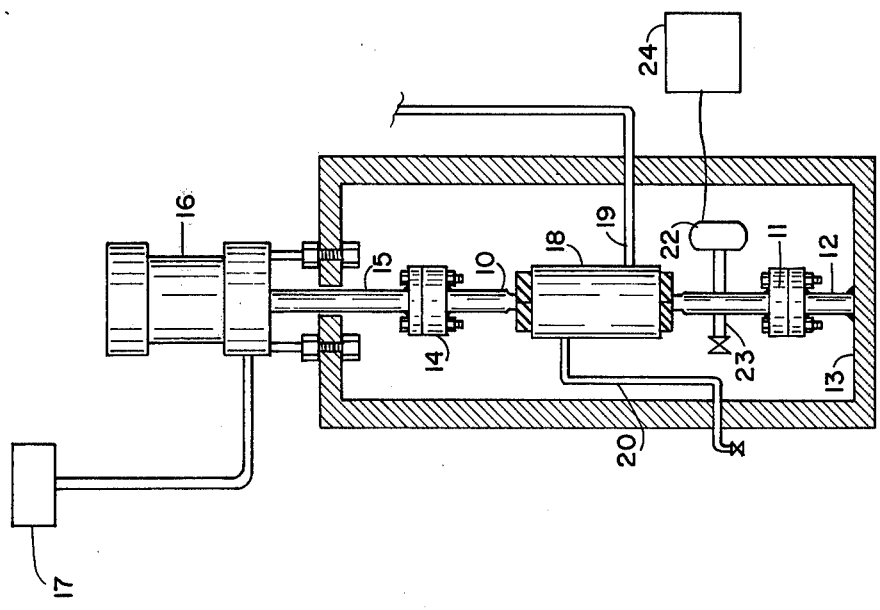
FIG. 1 is a schematic drawing of the apparatus of this invention.

The apparatus according to the preferred embodiment of the invention is illustrated in FIGS. 1 and 2. As shown therein, a test probe 10 is mounted with one end 11 secured by bolts to a holding means shown as a post 12 attached to a frame 13. The frame 13 is in turn firmly secured to any suitable support (not shown) for maintaining the overall apparatus in position. The upper end 14 of the test probe 10 is secured by bolts to a load-applying piston 15 extending from a load cylinder 16. The operation of piston 15 is controlled by control unit 17 which may include conventional instrumentation such as a timer, valve means, and a source of pressurized fluid. The function of the control unit 17 is to apply a cyclical tension load to the test probe 10, acting through load cylinder 16 and piston 15. Alternatively, a cyclic load could be applied to test probe 10 by any of several mechanisms readily available to an operator.

A jacket 18 surrounds a portion of the test probe 10, and is equipped with an inlet 19 and an outlet 20 to enable circulation of a corrosive fluid, with or without an inhibitor, over the portion of the test probe surrounded by jacket 18. Upper and lower closure members or stoppers complete the chamber provided by jacket 18 around probe 10. As explained in detail in the above-noted U.S. Pat. No. 3,942,546, a corrosive fliud flowing over test probe 10 results in corrosion at the surface of the test probe. This corrosion is manifested by generation of hydrogen atoms at the surface of the test probe. The test probe is hollow, and is evacuated to a very high vacuum, under which condition some of the hydrogen atoms generated at the outer surface of the test probe permeate through the test probe wall into the hollow center portion thereof.

As seen in FIG. 2 of the drawings, test probe 10 has a hollow chamber 21 which is in fluid communication with a getter-ion pump 22. Details of the construction and operation of getter-ion pumps are well known to those skilled in the art, and are described comprehensively in U.S. Pat. No. 3,942,546. In essence, the getter-ion pump 22 "pumps out" the hydrogen atoms which have permeated through the wall of the test probe 10, and the amount of hydrogen which has permeated the probe wall is reflected in the current reading on the current indicator connected to the ion pump. The current levels for this type of equipment are quite low, but are easily measured by available equipment.

The test probe 10 may be made of any suitable hydrogen permeable material, but one variable in the test procedure can be eliminated by making the probe from the specific metal which is used in the particular application for which the inhibitor is being considered. For example, a piece of sucker rod material may be cut and machined to include a chamber 21 and then attached to post 12 and piston 15 and utilized as the probe.

The operation of the apparatus will now be briefly described. A probe 10 is formed from the material to be tested, such as a section of sucker rod material. One end of the probe is fastened to post 12 which is attachd to frame 13. The other end of the probe 10 is attached to piston 15 extending from load cylinder 16 such that a cyclical tension load determined by control unit 17 can be applied to probe 10. Probe 10 is first evacuated by a vacuum pump connected through roughing vacuum outlet 23 in communication with chamber 21 of the probe. After the rough vacuum is obtained, the ion pump 22 is operated to further reduce the pressure within chamber 21. A corrosive fluid is circulated over the outer wall of the probe by flowing same into inlet 19 and out from outlet 20 of jacket 18 surrounding a portion of the probe 10. The corrosive fluid includes an inhibitor to be tested. A cyclic loading is applied to the probe by load cylinder 16 acting through piston 15 attached to the upper end of the probe. During the time that control unit 17 is causing a cyclic tension load to be applied to the probe, the amount of corrosion occuring at the surface of the probe in contact with the corrosive fluid is indicated by the current reading on an indicator 24 of the ion pump 22. A high current reading is indicative of a high level of fatigue corrosion, whereas a low current reading is indicative of a low level of fatigue corrosion under the applied test conditions. The reading can be obtained quite rapidly, and conditions can be varied to determine their effect upon the rate of corrosion. For example, the inhibitor can be changed, or the amount of inhibitor can be varied. Also, the level and frequency of the applied load can be varied, as can the composition and termperature of the corrosive fluid being tested. This operation provides two important advantages over previously available testing operations. The corrosion rate can be measured while the probe is under stress, and the measurement can be obtained without the necessity of testing the probe to destruction.

The apparatus of this invention can be modified by adding a second hydrogen probe and ion pump in the circuit whereby the corrosive fluid and inhibitor being tested can be simultaneously passed over a second unstressed probe to provide an indication of the corrosion rate for the probe in an unstressed condition. Comparison of the readings for the unstressed probe and the stressed probe can provide an indication of the effect of stress upon the material in question.

The stress need not necessarily be a tension load, as cyclic torsional or bending loads could be applied to the test probe by appropriate modification of the apparatus. Also, pulsating pressure stress could be applied to the test probe with appropriate equipment.

In order to evaluate the usefulness of the apparatus and method of this invention, the results obtained utilizing the invention were compared with the results obtained with some commercial corrosion inhibitors for which corrosion fatique data had previously been obtained by testing specimens to destruction utilizing the procedure described in U.S. Pat. No. 3,427,873.

EXAMPLE I

In this test, the effectiveness of the inhibitors in an $H_2S$ saturated brine was first determined by the weight loss method, and then by the technique described in U.S. Pat. No. 3,427,873. The results are tabulated in Table I.

Table I

| | Corrosion and Corrosion Fatigue Performance of Inhibitors | |
|---|---|---|
| Inhibitor | Corrosion Rate Mils/year | Corrosion Fatigue Life-Cycles |
| None | 50 | 760,000 |
| KP-106 | 2.0 | 12,000,000 |
| K-700 | 3.0 | 1,100,000 |

EXAMPLE II

The effectiveness of the corrosion inhibitors tested in Example I was then determined by the stressed probe technique utilizing the apparatus of this invention and the same corrosive environment used in Example I.

Simultaneously, similar measurements were obtained for an unstressed probe. The hydrogen probe current is indicative of the corrosion rate. The results of this test are tabulated in Table II.

Table II

| Hydrogen Probe Evaluation of Inhibitors | | |
|---|---|---|
| | Hydrogen Probe Current - $\mu A$ | |
| Inhibitor | Stressed Probe | Unstressed Probe |
| KP-106 | 11 | 3 |
| K-700 | 25 | <1 |

As seen from the above Tables, inhibitor KP-106 was slightly more effective than inhibitor K-700 by the weight loss method, was much more effective in the extended test to actual destruction of the test specimen, and was much more effective by the stressed probe method of this invention. Utilizing the hydrogen probe techinque of this invention, with the exception that the probe was not stressed, resulted in an inaccurate indication of effectiveness.

Summarizing the above test, the method and apparatus of this invention, utilizing a stressed probe, showed good correlation with the results obtained by an extended test to destruction of the test specimens, whereas a similar method utilizing an unstressed probe gave results which were not in accordance with the actual results obtained during the test to destruction. Thus, the method and apparatus of this invention, utilizing a stressed probe, provide a means for obtaining a rapid and reliable indication of the effectiveness of a particular inhibitor in a given situation, compared to the results obtained by actual test to destruction, and enable an operator to obtain results indicative of inhibitor effectiveness in a much shorter time than is required to test the specimen to failure as has been previously necessary.

It will be appreciated that many variables must be considered in analyzing results obtained by the method and apparatus of this invention, but it has been demonstrated that an indication of inhibitor effectiveness in a given situation can be obtained much more quickly than has been previously possible when test specimens were tested to failure.

What is claimed is:

1. Apparatus for determining the effectiveness of a corrosion fatique inhibitor comprising:
   a. a test probe having an evacuatable chamber, said test probe being formed of a metallic material which is permeable to hydrogen atoms;
   b. holding means for holding one end of said test probe;
   c. means for applying a cyclical stress to said test probe;
   d. a jacket including an inlet and an outlet, said jacket surrounding a portion of said test probe and a portion of said evacuatable chamber such that a fluid circulated through said jacket contacts the test probe;
   e. ion pump in fluid communication with said evacuatable chamber; and
   f. means for indicating the current in the ion pump as an indication of the amount of hydrogen permeating through the test probe into the evacuatable chamber thereof.

2. The apparatus of claim 1 wherein said means for applying a cyclical stress comprises a reciprocating piston connected to the other end of said test probe.

3. The apparatus of claim 2 wherein the means for applying a cyclical stress includes a fluid operated piston-and-cylinder means adapted to cyclically apply a tension load to said test probe.

4. A method for determining the effectiveness of a corrosion fatique inhibitor comprising:
   a. providing a test probe having a chamber therein;
   b. maintaining a vacuum in said chamber;
   c. passing a corrosive fluid containing an inhibitor over the test probe;
   d. applying a cyclical stress to said test probe;
   e. providing an ion pump in fluid communication with said chamber; and
   f. determining an indication of the amount of hydrogen permeation into said chamber by reference to the current in said ion pump.

5. The method of claim 4 wherein said cyclical stress is a cyclical tension load.

* * * * *